United States Patent
Wang et al.

(10) Patent No.: US 6,255,412 B1
(45) Date of Patent: Jul. 3, 2001

(54) POLYMERIZATION OF A STICKY POLYMER IN THE PRESENCE OF A TREATED CARBON BLACK

(75) Inventors: Weidong Wang, Piscataway; Kevin Joseph Cann, Rocky Hill, both of NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/343,169

(22) Filed: Jun. 29, 1999

(51) Int. Cl.$^7$ .................................................. C08F 2/34
(52) U.S. Cl. ........................ 526/88; 526/74; 526/194; 526/348; 526/901; 526/89; 526/335; 526/336; 524/496
(58) Field of Search .................. 526/74, 88, 194, 526/348, 901, 89, 335, 336; 524/496

(56) References Cited

U.S. PATENT DOCUMENTS

| | | | |
|---|---|---|---|
| 4,994,534 | 2/1991 | Rhee et al. | 526/88 |
| 5,086,132 | 2/1992 | Joyce | 526/74 |
| 5,162,463 | 11/1992 | Baker et al. | 526/74 |
| 5,200,477 | * 4/1993 | Baker et al. | 526/74 |
| 5,304,588 | 4/1994 | Boysen et al. | 523/204 |
| 5,453,471 | 9/1995 | Bernier et al. | 526/68 |
| 5,652,304 | 7/1997 | Calderon et al. | 526/142 |
| 5,763,541 | 6/1998 | Wang et al. | |
| 5,858,903 | 1/1999 | Sylvester et al. | 502/118 |
| 5,877,109 | 3/1999 | Reichert et al. | 502/117 |

FOREIGN PATENT DOCUMENTS

| | | |
|---|---|---|
| 0657647A1 | 6/1995 | (EP) . |
| 9604322 | 2/1996 | (WO) . |
| 9604323 | 2/1996 | (WO) . |
| 9637546 | 11/1996 | (WO) . |
| 9834960 | 8/1998 | (WO) . |

OTHER PUBLICATIONS

Gajewski et al. Chemical Modification of The Surface of Carbon Black with The Aid of the Sulfurating Agents and Its Influence on the Process of Reinforcing of The Amorphous Polyenes, Oct. 1979.*

Article, M. Gajewski and T. Prot, Radom (Poland), KGK Kautschuk Gummi Kunststoffe 47, Jahrgang, Nr. 8/94, "Correlation Between Crosslink Densty And Properties of Rubber Containing Chemically Modified Carbon Black" pp. 574–577.

Article, M. Gajewski, H. Jankowska, A. Swiatkowski, S. Zietek, Proc. Int. Rubber Conf. 1979 Venice, Italy Oct. 3–6, 1979, Chemical Modficiation Of The Surface Of Carbon Black With The Aid Of The Sulfurating Agents And Its Influence On The Process Of Reinforcing Of Amorphous Polyenes, pp. 101–110.

Article, M. Gajewski, Nesz Nauk–Wyzszeo Szkoly Inzynierskiej W Radomiu Materialoznawstwo Chemiczne I Technologia Obuwia NR 12, Wlasciwosci Usieciowanych Polienow Zawierajacych Sadze Aktywna O Powierzchni Zmodyfikowanej Chemicznie ZA Pomoca Donorow Siarki, 1989, pp. 87–100.

* cited by examiner

*Primary Examiner*—David W. Wu
*Assistant Examiner*—William Cheung
(74) *Attorney, Agent, or Firm*—James H. Dickerson, Jr.

(57) ABSTRACT

There is provided a polymerization of a sticky polymer in the presence of a catalyst under polymerization conditions using carbon black as the inert particulate material, the improvement comprises conducting said polymerization in the presence of a carbon black that has been treated with a sulfur donor and/or an oxidizing agent.

5 Claims, 3 Drawing Sheets

Effect of purging time and purging temperature on butadiene residue in CB: CB N550 purged at 60, 80, 100 and 120°C.

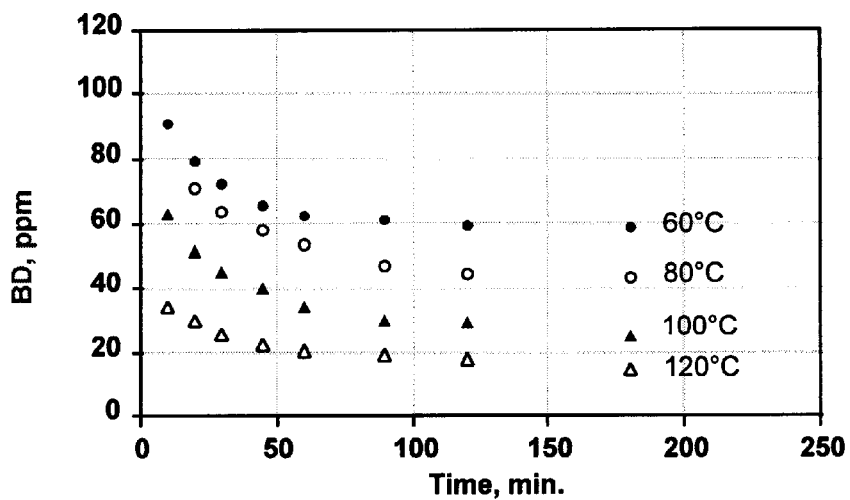
Figure 1. Effect of purging time and purging temperature on butadiene residue in CB: CB N550 purged at 60, 80, 100 and 120°C.
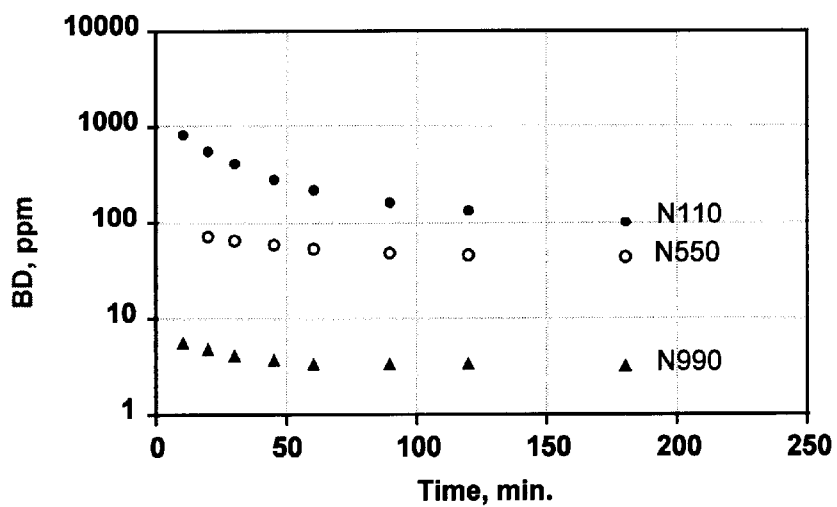
Figure 2. Desorption of butadiene from CB surface: N110, N550 and N990 purged at 80°C.

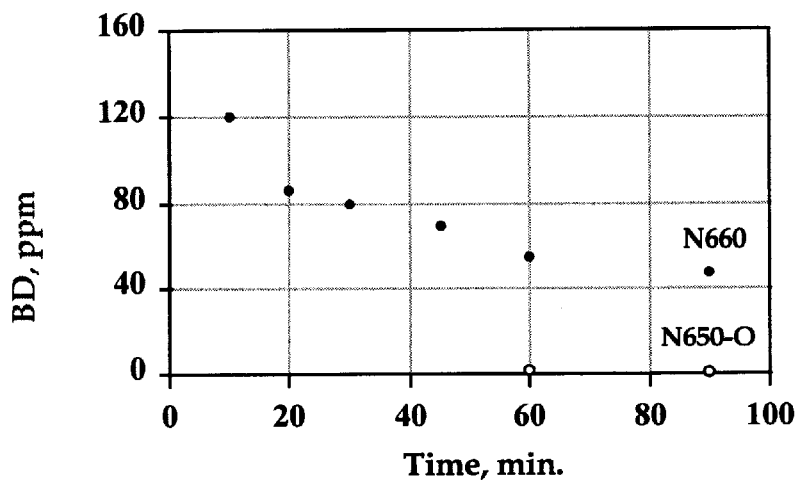
Figure 3. Oxidized CBs have low butadiene residue: CB N660 and oxidized CB N650-O.
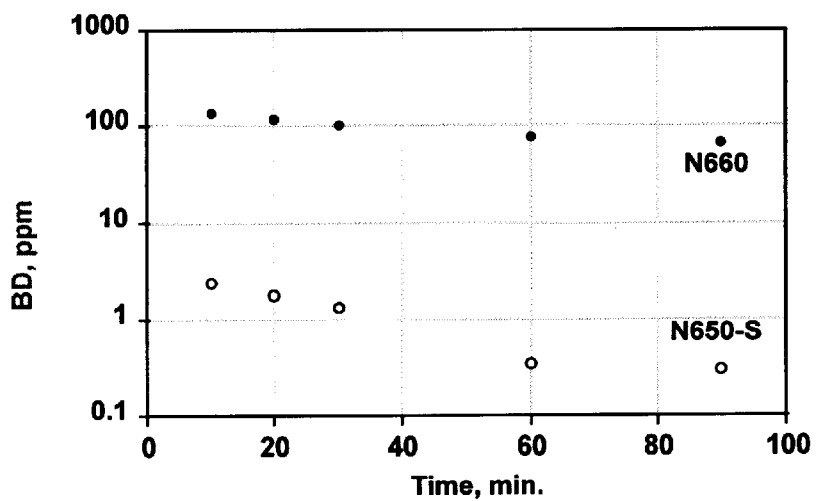
Figure 4. Butadiene adsorption decreases upon sulfur modification: N650-S: sulfur modified CB.

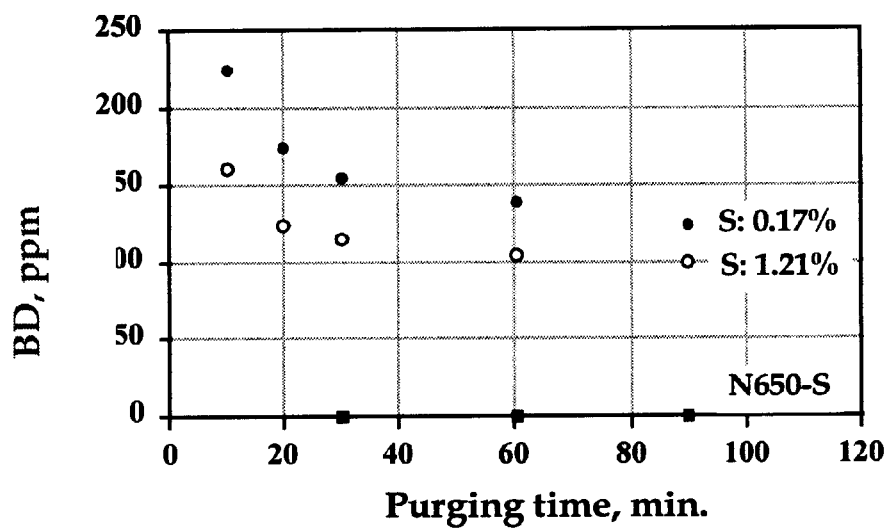
Figure 5. CB rich in sulfur as produced by CB manufacturer have high butadiene residue.

POLYMERIZATION OF A STICKY POLYMER IN THE PRESENCE OF A TREATED CARBON BLACK

FIELD OF THE INVENTION

The present invention relates to the polymerization of a sticky polymer in the presence of an inert particulate material. More particularly, the invention relates an improvement in the polymerization of a sticky polymer, which improvement comprises polymerizing in the presence of a carbon black that has been treated with a sulfur donor and/or oxidizing agent.

BACKGROUND OF THE INVENTION

It has been disclosed that sticky polymers such as ethylene/propylene/diene monomer (EPDM) and polydienes such as polybutadiene (BR), polyisoprene (IR), and styrene-butadiene rubber (SBR) can be produced in gas phase polymerization processes. Such processes are disclosed, for example, in U.S. Pat. Nos. 4,994,534; 5,304,588; 5,453,471; 5,652,304; 5,858,903; 5,877,109; EP 0 657 647; and WO 96/04322 and 04323.

In general, a sticky polymer is defined as a polymer being particulate at temperatures below the sticking or softening temperature but forming agglomerates at temperatures above its sticking or softening temperature. In order to maintain such forming polymers in a fluidized state in a gas phase polymerization, an inert particulate material such as carbon black, silica, talc, clay, activated carbon black, and mixtures thereof can be employed. These inert particulate materials also serve to coat the polymer rendering it a non-sticky, free-flowing granule or particle as it exits the polymerization reactor.

More recently, it has been disclosed in WO 98/34960 that a "modified carbon black" can be employed for these purposes. A "modified carbon back" is defined on pages 4–5 of the reference. For the most part, this definition defines a modified carbon black as a silicon-treated or silica-coated carbon black. However, part (c) of the definition discloses that the modified carbon black can be "a carbon black having an attached organic group(s)." According to the reference (pages 10–18), this organic group is attached via the reaction of a diazonium salt with a carbon black. Such a substituted organic group imparts water dispersibility (pages 17–18). Other organic groups, according to the reference (pages 18–19), can include attached aromatic sulfide and aminophenyl groups. It is further suggested in this reference (pages 20–21) that the use of these modified carbon blacks in a gas phase polymerization will produce a polymer product containing them which, in turn, will result in an article (e.g., hose or tire) having improved properties. Gas phase polymerizations employing these modified carbon blacks and the suggested improvements are not demonstrated.

Additionally, WO 98/34960 does not address the problems discovered and solved by the inventors of this invention. In the present invention, the inventors have found that monomers (especially dienes, as well as any other organic species) have a strong tendency to be adsorbed by carbon black that is employed in a polymerization as the inert particulate material (aka fluidization aid). When this occurs, the monomer can also be absorbed in the polymer product. First, this phenomenon makes it extremely difficult to purge or otherwise remove unreacted monomer from the polymer in post reactor processing. That is, it is necessary to purge unreacted monomer for much longer periods of time under more stringent conditions to remove it because of its potential exposure to the environment and/or to humans. Second, the presence of a monomer residue adsorbed on the surface of the carbon black in the polymer product and/or the stress imposed in extended purging may reduce the polymer's carbon black reinforcing ability in a compounded article.

Thus, for these reasons, there needs to be provided a carbon black that not only can coat the forming polymer in a polymerization such as in a gas phase reactor so that it is fluidizable, but the carbon black must also be one that does not readily adsorbed or retain monomer such that an onerous amount of time is required for purging or removal. The present invention provides a way to reduce the retention/adsorption of undesirable monomer in the polymer product.

BRIEF DESCRIPTION OF THE DRAWINGS

FIG. 1 demonstrates that the amount of monomer (e.g., butadiene) residue in the head space decreased with an increase in carbon black purging time, but remained higher than the desired level (e.g., of less than about 1 ppm).

FIG. 2 demonstrates that the amount of monomer (e.g., butadiene) residue in the head space after purging (in nitrogen at 80° C.) varied depending on the type of carbon black used and was still higher than the desired residue level (e.g., of less than about 1 ppm).

In FIG. 3 it is shown that a carbon black treated in accordance with the invention (i.e., oxidized with nitric acid in water) resulted in lower monomer residue.

And, in FIG. 4, a sulfur modified carbon black in accordance with the invention likewise resulted in the desired lower monomer residue as compared to the untreated carbon black.

FIG. 5 demonstrates that a sulfur containing carbon black obtained from a carbon black manufacturer did not exhibit the desired performance as the treated carbon black of the invention set forth in FIG. 4.

SUMMARY OF THE INVENTION

There is provided a polymerization of a sticky polymer in the presence of a catalyst under polymerization conditions using carbon black as the inert particulate material, the improvement which comprises conducting said polymerization in the presence of a carbon black that has been treated with a component selected from the group consisting of a sulfur donor, an oxidizing agent, and a mixture thereof. In a preferred embodiment, the treating component is elemental sulfur, a sulfur-donor compound, nitric acid, nitric oxide-air, ozone, hot air, or a mixture thereof. The novel process using the treated carbon black results in shorter/easier purging of a sticky polymer to remove/reduce undesirable monomer levels, as well as, for preventing or reducing the adsorption of a monomer into or on carbon black during a polymerization of a polymer. This especially has utility in the production of sticky polymers in gas phase processes.

There is also provided a treated carbon black having reduced monomer retention capacity. The treated carbon black is obtained by contacting a carbon black with a component selected from the group consisting of sulfur donor, an oxidizing agent, and a mixture thereof.

DETAILED DESCRIPTION OF THE INVENTION

This invention provides the treating of a carbon black with a component that is a sulfur donor or oxidizing agent. Preferably, the carbon black is treated with elemental sulfur, a sulfur-donor compound, nitric acid, nitric oxide-air, ozone, hot air heated to 300 to 700° C., or a mixture of them. These treated carbon blacks have a very low monomer (especially diene) adsorption/release, usually 50 to 100 times lower than carbon black that has not been treated as in the present invention.

Carbon blacks suitable for treatment can be obtained commercially or prepared using well-known processes and techniques such as those taught in PCT/US98/02518. Typically, such carbon blacks are produced in a modular or staged furnace carbon black reactor. To produce carbon black in such a reactor, hot combustion gases are generated in a combustion zone by contacting a liquid or gaseous fuel with a suitable oxidant stream such as air, oxygen, or a mixture thereof. Among fuels suitable for use in contacting the oxidant stream in the combustion zone of the reactor to generate the hot combustion gases are included any readily combustible gas, vapor of liquid streams such as natural gas, hydrogen, methane, acetylene, alcohols, or kerosene. Generally, fuels having a high content of carbon-containing components (e.g., hydrocarbons) are used. Carbon blacks can be produced by the pyrolysis or partial combustion of any liquid or gaseous hydrocarbon usually from petroleum refinery sources such as decanted oils from catalytic cracking operations or by-products from coking operations and olefin manufacturing operations. The feedstock is converted (e.g., pyrolyzed) to carbon black and the carbon black particles formed are quenched (usually with water). After quenching, the carbon black is cooled and recovered by conventional means known to those skilled in the art. Recovered carbon black can optionally be subjected to a pelletization step.

Sulfur can be present in carbon black as it is produced during manufacturing. It can be present in one or more forms such as elemental sulfur, inorganic compounds, or organic sulfur compounds. Typically, it is present on the surface of the carbon black particles in an amount of up to 1% by weight based upon the total weight of the carbon black. However, carbon black particles rich in sulfur due to carbon black production did not significantly reduce monomer adsorption/release in the final polymer product in the present invention.

It was found that post-carbon-black-formation treatment with a sulfur and/or sulfur-donor compound significantly reduced monomer adsorption/release in the sticky polymer produced in a gas phase polymerization. That is, sulfur substituents fixed on the surface of the carbon black particles can be increased by treating carbon black after it has been formed with elemental sulfur and/or sulfur-donor compounds in accordance with the invention. This is accomplished by mixing carbon black with elemental sulfur or a sulfur-donor compound in amounts ranging from about 0.1 to 40% by weight based upon the total carbon black optionally in the presence of a solvent at a temperature ranging from about 25° C. to 1000° C. at ambient pressure or higher pressure. Sulfur-donor compounds employable in the present invention can include, for example, $H_2S$, $SO_2$, $CS_2$, $P_2S_5$, and $SOCl_2$. Solvents when employed in the present invention can include, for example, water, hydrocarbons, chlorinated hydrocarbons, ethers, alcohols, esters, etc. The solvent is removed by heating with purging and/or vacuum. Mixing time (or treatment time) can vary, and ranges from 0.1 to 24 hours. Depending on the targeted sulfur concentrations on the carbon black particles, the amount of sulfur or sulfur-donor compound used in the treatment can be adjusted such that the treated carbon black may have a small concentration (i.e., less than 1%) of free, unreacted sulfur or sulfur-donor compound. Such sulfur substituents can include sulfide, hydrosulfide, sulfone, sulfoxide, thiocarbonyl, and thiolactone. It has been found that the sulfur groups on CB surface may participate in cross-linking reaction in presence of accelerator and activator of cure package during the vulcanization, which contribute to the reinforcement of carbon black. On the one hand, the introduction of sulfur groups on the CB surface will decrease adsorption of butadiene on the surface, and on the other hand, sulfur groups may interact with butadiene in the purging process and prevent butadiene releasing to the head space.

In the present invention, carbon black can be oxidized after it is produced by treating or oxidizing it with strong oxidizing agents such as nitric acid, ozone, nitric oxide-air, hot air, or a mixture of them to raise the concentration of oxides on the surface of the carbon black.

When nitric acid is employed as the oxidizing agent, it can be added to the water employed in a carbon black pelletizing process followed by drying the pellets comprising the treated carbon black at an elevated temperature (50 to 400° C.) at ambient pressure or higher until the water content is less than 0.5 wt %. Carbon black particles can also be mixed with the nitric acid in a solvent (e.g., water) and dried before using the treated particles in a gas phase polymerization to produce a sticky polymer.

In the present invention, ozone can be employed to treat the carbon black particles. When ozone is employed, it is used in excess of a stoichiometric amount, carbon black particles are place in a vessel such as a fluidized bed container, and oxidized using ozone (or an ozone-containing gas) that is passed through and/or over the particles at room temperature or higher (i.e., temperatures ranging from about 25 to 200° C.) at ambient pressure for a few minutes (less than 1 hour).

The simplest and most preferred way to obtain a treated carbon black using an oxidizing agent is to heat the carbon black particles in hot air at high temperatures ranging from about 350 to 700° C. However, due to the thermal stability of the surface oxides obtained, the extent of oxidation is limited. When higher levels of oxidation on the surfaces of the carbon black particles is desired, the particles can be treated with a mixture of nitric oxide and air. This is preferably accomplished in a vessel such as a fluidized-bed in which nitric oxide (e.g., $NO_2$) is passed over and/or through the carbon black particles at temperatures ranging from 300 to 700° C. at ambient pressures or higher. Depending upon the desired degree of oxidation, this treatment can be accomplished in a few minutes up to several hours (up to 4 hours).

The surfaces of carbon black treated with an oxidizing agent of the invention may contain such oxide groups as hydroxyl, carboxyl, lactonic, quinonic, and mixtures of them.

The amount of oxide groups on the surfaces of the treated carbon black may vary depending upon the degree of oxidation to which the particles have been subjected. In general, the amount ranges from about 0.01 meq/g to 10 meq/g. Some oxidized carbon blacks such as Special Black-250 and Printex are commercially available from Degussa AG.

Polymerization Process. The treated carbon black as described above can be employed in any polymerization process utilized for employing a sticky polymer in the presence of a polymerization catalyst. Such processes can include solution, slurry, bulk, and gas phase processes.

Solution, slurry, and bulk processes are well known and disclosed, for example, in U.S. Pat. Nos. 3,386,983; 3,458,490; 3770,710; 4,098,980; 4,452,960; 5,086,132; and EPO 011184. In such processes the treated carbon black is mixed with one or more of the other ingredients, as for example in U.S. Pat. No. 5,086,132.

Preferably, a gas phase polymerization process is employed to produce a sticky polymer. The invention can be used for the gas phase polymerization of one or more alpha olefins, and optionally a diene (or diolefin) or the polymerization of a conjugated diene. Gas phase processes employable in the present invention can include so-called "conventional" gas phase processes, "condensed-mode," and, most recent, "liquid-mode" processes. In these processes, it may be desirable to include a scavenger in the reactor to remove adventitious poisons such as water or oxygen before they can lower catalyst activity.

Conventional fluidized processes are disclosed, for example, in U.S. Pat. Nos. 3,922,322; 4,035,560; 4,994,534; 5,304,588, and 5,317,036. Condensed mode polymerizations, including induced condensed mode, are taught, for example, in U.S. Pat. Nos. 4,543,399; 4,588,790; 4,994,534; 5,304,588; 5,317,036; 5,352,749; and 5,462,999. Liquid mode or liquid monomer polymerization mode is described in U.S. Pat. No. 5,453,471; and WO 96/04322 and 04323 (PCT/US95/09826 and 09827). Other processes that can be employed are disclosed in U.S. Pat. Nos. 5,652,304; 5,858,903; 5,877,109; and EP 0 657 647.

When the treated carbon blacks of the invention are employed as fluidization aids, they are used in amounts ranging from about 0.3 to about 80% by weight, preferably about 5 to 60%, most preferably 10 to 45%, based on the weight of the polymer produced.

The treated carbon black fluidization aid can be added to the reactor separately or mixed with all or a portion of one or more of the monomers and/or the catalyst. Treated carbon black can be introduced into the reactor at or near the top of the reactor, at the bottom of the reactor, or to the recycle line directed into the bottom of the reactor. Preferably, the treated carbon black fluidization aid is introduced at or near the top of the reactor or above the fluidized bed. It is generally preferred to treat (i.e., dry) the fluidization aid prior to entry into the reactor to remove traces of moisture and oxygen.

The use of inert particulate materials (e.g., carbon black) as fluidization aids in polymerization (especially gas phase polymerizations) typically produces a polymer having a core-shell configuration such as that disclosed in U.S. Pat. No. 5,304,588. However, this is not the only possible configuration especially for particles produced in non-gas phase processes. The polymer produced with one or more of these fluidization aids produces a resin particle comprising an outer shell having a mixture of a polymer and an inert particulate material, wherein the inert particulate material is present in the outer shell in an amount higher than 75% by weight based on the weight of the outer shell; and an inner core having a mixture of inert particulate material and polymer, wherein the polymer is present in the inner core in an amount higher than 90% by weight based on the weight of the inner core. These polymer particles are granular and free-flowing upon exiting the reactor and are produced by a fluidized bed polymerization process at or above the softening point of the sticky polymer.

The polymerizations can be carried out in a single reactor or multiple reactors, typically two or more in series, can also be employed. The essential parts of the reactor are the vessel, the bed, the gas distribution plate, inlet and outlet piping, at least one compressor, at least one cycle gas cooler, and a product discharge system. In the vessel, above the bed, there is a velocity reduction zone, and in the bed a reaction zone.

Generally, all of the above modes of polymerizing are carried out in a gas phase fluidized bed containing a "seed bed" of polymer which is the same or different from the polymer being produced. Preferably, the bed is made up of the same granular polymer that is to be produced in the reactor.

The bed is fluidized using a fluidizing gas comprising the monomer or monomers being polymerized, initial feed, make-up feed, cycle (recycle) gas, inert carrier gas (e.g., nitrogen, argon, or inert hydrocarbon having 2 to 12 carbon atoms such as ethane, propane, isopentane) and, if desired, modifiers (e.g., hydrogen). Thus, during the course of a polymerization, the bed comprises formed polymer particles, growing polymer particles, catalyst particles, and optional flow aids (fluidization aids) fluidized by polymerizing and modifying gaseous components introduced at a flow rate or velocity sufficient to cause the particles to separate and act as a fluid.

In general, the polymerization conditions in the gas phase reactor are such that the temperature can range from sub-atmospheric to super-atmospheric, but is typically from about 0 to 120° C., preferably about 40 to 100° C., and most preferably about 40 to 80° C. Partial pressure will vary depending upon the temperature of the polymerization, and it can range from about 1 to 300 psi (6.89 to 2,067 kiloPascals), preferably 1 to 100 psi (6.89 to 689 kiloPascals). Preferably, the gas phase process used in conjunction with the treated carbon black of the invention is conducted in a gas phase reactor or a semibatch gas phase reactor under reaction conditions such that at least a portion of at least one of the olefinic and/or diolefinic monomers present is maintained at or below its dew point temperature.

Dienes when employed in the production of sticky polymers can include: conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, 7-methyl-1,6-octadiene (MOD), vinylcyclohexene, dicyclopentadiene, butadiene, isobutylene, isoprene, ethylidene norbornene (ENB), and the like. For sticky polymers such as EPDM, ENB, MOD, 1,5-hexadiene, and dicyclopentadiene are most preferred.

The catalyst employed in the polymerization can contain a precursor, organoaluminum cocatalyst and promoter (optional). It can be supported (on an inert carrier material such as carbon black, silica, magnesia, alumina, and/or activated carbon) or unsupported (as a liquid or in a slurry, solution, or emulsion). The catalyst can be in the form of a prepolymer or sprayed dried (with or without a filler material). Typical catalysts precursors can, for example, include compounds employing a metallocene (e.g., containing a metal selected from the group consisting of titanium, hafnium, zirconium, and mixtures thereof) and/or compounds employing a transition or rare earth metal (e.g., containing a metal selected from the group consisting of nickel, cobalt, titanium, vanadium, neodymium, and mixtures thereof).

When a catalyst support is employed, it can be impregnated with one or more of the individual catalyst components (precursor, cocatalyst, promoter). Generally, the catalyst precursor is impregnated and the other components are introduced separately into the polymerization. If used, the support can be silica, alumina, carbon black, activated carbon, or polymeric material with silica being the most preferred. Examples of polymeric supports are porous crosslinked polystyrene and polypropylene. A typical silica or alumina support is a solid, particulate, porous material essentially inert to the polymerization. It is used as a dry powder having an average particle size of about 10 to about 250 microns, preferably about 30 to 100 microns; a surface area of at least 200 square meters per gram, preferably at least about 250 square meters per gram; and a pore size of at least about 100 Angstroms, preferably at least about 200 Angstroms. Impregnation of the catalyst precursor or other component of the catalyst system onto a support such as silica is well known and can be accomplished, for example, by mixing the precursor and silica gel in an inert solvent followed by solvent removal under reduced pressure.

Unreacted monomer including unreacted diene encountered in gas phase processes can be purged by known methods such as those described, for example, in U.S. Pat. Nos. 4,758,654; 5,191,062; 5,292,863; 5,478,922; 5,688,910; and U.S. Ser. No. 09/098,479.

The polymers produced by the invention are designated as "sticky polymers." Sticky polymers are defined in U.S. Pat. Nos. 4,994,534 and 5,304,588. A sticky polymer is defined as a polymer which, although particulate at temperatures below the sticking or softening temperature, agglomerates at temperatures above such temperature. The agglomeration may be spontaneous or occur on settling. A polymer may be inherently sticky due to its chemical or mechanical properties or pass through a sticky phase during the production cycle. Although many variables influence the degree of stickiness of the polymer, it is predominantly governed by the temperature (sticking) and the crystallinity of the resin. Higher temperature of the resin increases stickiness. Less crystallinity, or conversely more amorphous or elastomeric the resin, the greater the tendency to agglomerate or stick. In general, a sticky polymer has a density of less than 0.915 when produced at temperatures above its melting/softening temperature.

Examples of polymers that can be produced using the treated carbon black and process of the invention include ethylene-propylene rubbers; ethylene-propylene-diene rubbers; polybutadiene rubbers; polyisoprenes; high ethylene content propylene-ethylene block copolymers; poly(1-butene) (when produced under certain reaction conditions); polypropylenes; polyethylenes; very low density (low modulus) polyethylenes, i.e., ethylene butene rubbers or hexene containing terpolymers; especially ethylene-propylene-ethylidenenorbornene terpolymer, ethylene-propylene-hexadiene terpolymer, and ethylene-propylene-octadiene terpolymer.

The polymer particles produced by the process of the invention comprise polymer and treated carbon black. Typically the polymer particle has a mass of polymer in its core and a shell comprising treated carbon black and/or a mixture of polymer and treated carbon black. It should be understood that the polymer particle does not necessarily have to have a core shell configuration but rather the carbon black can be distributed through out the particle. The polymer particles so produced are granular and free-flowing and can be used to make molded and extruded articles such as tires, roofing material, hoses, and cable.

All references herein are incorporated by reference.

Whereas the scope of the invention is set forth in the appended claims, the following examples illustrate certain aspects of the present invention. The examples are set forth for illustration and are not necessarily to be construed as limitations on the invention, except as set forth in the claims. Throughout the specification all parts and percentages are by weight unless otherwise stated.

EXAMPLE

Purging. In all examples, carbon black particles (10 g) were saturated with butadiene for at least 16 hours. Purging was carried out in a 250-ml jacketed column in which the temperature was controlled by heating an oil such as silicone oil in at temperatures set forth in the Figures using nitrogen (1 liter/min).

Method for Measuring Adsorption/Desorption Capacity of Carbon Black. The purged carbon black was sealed in a 20 ml GC (gas chromatography) head space vial, in which butadiene redistributed between solid phase and head space. An equilibrium of monomer concentration at 150° C. was measured by GC analysis. The measured butadiene in the head space and is normalized by the carbon black sample weight in the vial as follows:

$$BD \text{ Residue, ppm} = \frac{BD \text{ in head space, } \mu g}{CB \text{ weight, g}}$$

Example 1 (Comparative)

Butadiene residue level was reduced by purging. FIG. 1 shows an example of CB N550 purged at 60, 80, 100 and 120 ° C. The butadiene residue decreased with the purging time especially during the first few minutes then slowly afterwards. The decrease seemed to be significant for the first 60 minutes. Afterwards, it tended to be constant until approximately 180 minutes. Purging temperature (60 to 120° C.) was a very important factor for reduction of the butadiene residue. High temperature purging reduced significantly BD residue. However, the final butadiene residue was still much higher than the desired level. The adsorption of butadiene on carbon black was a function of surface properties. The high reinforcing, high surface area carbon black held more butadiene than that of low reinforcing big particle size carbon black.

FIG. 2 shows the BD residue on different commercially available carbon blacks (CB N110, N550 and N990) after being purged at 100 ° C. and measured at 150 ° C. N110 was a high reinforcing carbon black particle which meant that it had a high surface area high surface activity. N990 was a low reinforcing carbon black with a low surface area. The butadiene residue level decreased with increased purging time. And the high reinforcing carbon black had higher residues because of its high surface area (N110>N550>N990). However, the butadiene residue levels of all the different carbon blacks remained higher than the desired level.

Example 2. Preparation of Oxidized Carbon Black (CB)

Oxygen containing functional groups widely exist on the CB surface, but the concentration was relatively low. The total oxygen content was 0.2 to 0.3% by elemental analysis. Oxidized CB was obtained by mixing carbon black particles (25 g of N660) with nitric acid (400 ml 6N) and heating the mixture at 100° C. or approximately 3–4 hours. After treatment, the treated carbon black particles were separated from the liquid by decantation and washed with distilled water until the wash water tested neutral. The treated washed carbon black was dried in a vacuum. It had an average oxygen content of 4% as measured by ESCA (Electron Spectroscopy for Chemical Analysis). FIG. 3 shows the comparison of butadiene residue on untreated carbon black (N650) and the treated carbon black (N650-O) purged at 80° C. and measured at 150° C. This clearly indicated the significant reduction of butadiene residue level due to the presence of oxygen functional groups on the CB surface. These oxygen-containing groups of the invention may act as a butadiene scavenger to reduce the butadiene residue on the carbon black surface.

Example 3. Preparation of Sulfur Modified Carbon Black

Carbon black (16 g N650) was pre-mixed with 4 g of elemental sulfur in a vessel which was then heated to 400° C. in argon for 2 hours. The product was extracted with CS2 in a Soxhlet® to remove excess free sulfur in the mixture after reaction. The extracted carbon black was dried in a vacuum at 110° C. The ESCA analysis indicated the sulfur content was about 1% on the surface, which was chemically bound to the CB graphitic ring.

Here again, the sulfur-modified CB N650 (N650-S) had a very low butadiene adsorption that decreased with the purging time (FIG. 4). The butadiene levels were very low compared with those of untreated CB That is, the treated sulfur-modified carbon black (N650-S) had a lower butadiene residue (0.2 ppm) than the untreated carbon black (N650) (60 ppm).

In contrast, CB rich in sulfur as produced by a CB manufacturer did not exhibit this performance (FIG. 5). These sulfurs came from a feed stock composed of chemically bonded organic sulfur. These sulfur groups were formed at very high temperature, and their reactivity was much lower than those formed at relatively low temperature (400° C.).

What is claimed is:

1. In a polymerization of a sticky polymer in the presence of a catalyst under polymerization conditions, using carbon black as an inert particulate material, the improvement which comprises conducting said polymerization in the presence of a carbon black that has been treated with a sulfur donor, $H_2S$, $SO_2$, $CS_2$, $P_2S_5$, $SOCl_2$ or any mixture thereof; nitric acid; ozone or an ozone containing gas or hot air.

2. The polymerization of claim 1 wherein the treating component is selected from the group consisting of elemental sulfur, a sulfur-donor compound, nitric acid, nitric oxide-air, ozone, and hot air.

3. The polymerization of claim 1 wherein the carbon black is treated with elemental sulfur or a sulfur-donor compound in amounts ranging from 0.1 to 40% by weight based upon total carbon black optionally in the presence of a solvent at a temperature ranging from about 100 to 1000° C. at ambient or higher pressure.

4. The polymerization of claim 1 wherein the polymer produced is selected from the group consisting of ethylene-propylene-diene terpolymer rubber, polybutadiene, polyisoprene, and styrene-butadiene rubber.

5. The polymerization of claim 1 wherein said polymerization is conducted in a gas phase process.

* * * * *